United States Patent [19]

Heneine et al.

[11] Patent Number: 6,136,534
[45] Date of Patent: *Oct. 24, 2000

[54] METHODS FOR SENSITIVE DETECTION OF REVERSE TRANSCRIPTASE

[75] Inventors: Walid Heneine, Decatur; Thomas M. Folks, Lithonia; William M. Switzer, Stone Mountain, all of Ga.; Shinji Yamamoto, Shimizukamei-machi, Japan

[73] Assignee: The United States of America as represented by the Department of Health and Human Services, Washington, D.C.

[*] Notice: This patent is subject to a terminal disclaimer.

[21] Appl. No.: 09/123,012

[22] Filed: Jul. 27, 1998

Related U.S. Application Data

[63] Continuation of application No. 08/763,762, Dec. 11, 1996, Pat. No. 5,849,494, which is a continuation-in-part of application No. 08/379,851, Jan. 27, 1995, abandoned.

[51] Int. Cl.⁷ .............................. C12Q 1/68; C12P 19/34; C07H 21/02; C07H 21/04
[52] U.S. Cl. ........................... 435/6; 435/91.2; 536/23.1; 536/24.3; 536/24.31; 536/24.33
[58] Field of Search ..................... 435/6, 91.2; 536/23.1, 536/24.3, 24.31, 24.33

[56] References Cited

U.S. PATENT DOCUMENTS

| | | |
|---|---|---|
| 4,707,439 | 11/1987 | Seto et al. . |
| 5,066,782 | 11/1991 | Montagnier et al. . |
| 5,124,327 | 6/1992 | Greenlee et al. . |
| 5,320,958 | 6/1994 | Inouye et al. ............................ 435/194 |
| 5,360,714 | 11/1994 | Seeger ......................................... 435/6 |
| 5,407,800 | 4/1995 | Gelfand et al. .............................. 435/6 |
| 5,434,070 | 7/1995 | Inouye et al. ............................ 435/194 |
| 5,508,166 | 4/1996 | Tanno et al. ................................. 435/6 |
| 5,527,819 | 6/1996 | Williams et al. . |
| 5,541,334 | 7/1996 | Kempf et al. . |
| 5,559,256 | 9/1996 | Gordon et al. . |
| 5,576,117 | 11/1996 | Fridland et al. . |
| 5,591,770 | 1/1997 | Boyd et al. . |
| 5,597,926 | 1/1997 | Kempf et al. . |
| 5,807,669 | 9/1998 | Schübach et al. ........................... 435/4 |
| 5,849,494 | 12/1998 | Heneine et al. ............................. 435/6 |

FOREIGN PATENT DOCUMENTS

| | | |
|---|---|---|
| 372904 | 6/1990 | European Pat. Off. . |
| 392459 | 10/1990 | European Pat. Off. . |
| 289603 | 5/1991 | Germany . |
| WO 9314221 | 7/1993 | WIPO . |
| WO 9323560 | 11/1993 | WIPO . |
| WO 9428115 | 12/1994 | WIPO . |
| WO96/12809 | 5/1996 | WIPO . |
| WO 9623076 | 8/1996 | WIPO . |

OTHER PUBLICATIONS

Palmenberg et al, "The nucleotide and deduced amino acid sequences of the encephalomyocarditis viral polyprotein coding region", Nucleic Acid Res. 12(6):2969–2985, 1984.

Stratagene Catalog, p. 39, 1988.

Silver et al, "An RT–PCR assay for the enzyme activity of reverse transcriptase capable of detecting single virions", Nucleic Acid Research, 21(15):3593–3594, 1993.

Pyra et al, Ultrasensitive retrovirus detection by a reverse transcriptase assay based on product enhancement, Proc. Natl. Acad. Sci. USA 91:1544–1548, Feb. 1994.

Respess, R., et al., "Detection of HIV–1 group M and O virus–with a single PCR primer/probe set," *3rd Cof. Retro and Opportun. Infect.*, p. 154 (Jan 28–Feb. 1, 1996).

Janssens, W. et al., "Diagnosis of HIV–1 group O infection by polymerase chain reaction," *The Lancet*, vol. 346, pp. 451–452 (Aug. 12, 1995).

Gurtler, L.G., et al., "Reactivity of five anti–HIV–1 subtype O specimens with six different anti–HIV screening ELISAs and three immunoblots," *J. Virol. Meth.*, vol. 51, pp. 177–184 (1995).

Heneine, W., et al., "Detection of Reverse Transcriptase by a Highly Sensitive Assay in Sera from Persons Infected with Human Immunodeficiency Virus Type 1," *J. Infect. Dis.*, vol. 171, pp. 1210–1216 (1995).

Silver, J., et al., "An RT–PCR assay for the enzyme activity of reverse transcriptase capable of detecting single virions," *Nucleic Acids Research*, vol. 21 No. 15, pp. 3593–3594 (1993).

Heinemeyer, Thomas, et al., "A sensitive method for the detection of murine C–type retrovirses," *J. Virol. Meth.*, vol. 63, pp. 155–165 (1997).

"Identification of HIV–1 Group O Infection—1996," *JAMA*, vol. 276, No. 7, pp. 521–522 (Aug. 21, 1996).

Irving, J.M. et al., "A Reverse Transcriptase–Polymerase Chain Reaction Assay for the Detection and Quantitation of Murine Retroviruses," *Bio/Technology*, vol. 11, pp. 1042–1046 (Sep. 1993).

Im, G. et al., "Identification of the Amino Acid in the Human Immunodeficiency Virus Type 1 Reverse Transcriptase Involved in the Pyrophosphate Binding of Antiviral Nucleosid Triphosphate Analogs and Phosphonoformate," *Biochem. Pharm*, vol. 46, No. 12, pp. 2307–2313 (1993).

(List continued on next page.)

*Primary Examiner*—Jeffrey Fredman
*Attorney, Agent, or Firm*—Jones & Askew, LLP

[57] ABSTRACT

The present invention provides a method for detecting the presence of a retrovirus in a biological sample comprising the steps of: a) contacting the biological sample with an RNA template and a complementary DNA primer under conditions whereby the RNA template and the DNA primer will anneal and a DNA strand will be synthesized as an extension from the DNA primer if reverse transcriptase is present in the sample; b) amplifying the synthesized DNA; and c) detecting the amplification of the synthesized DNA, the amplification of the synthesized DNA indicating the presence of reverse transcriptase in the biological sample, thus indicating the presence of a retrovirus in the biological sample.

15 Claims, No Drawings

OTHER PUBLICATIONS

Yamamoto et al., "Highly sensitive qualitative and quantitative detection of reverse transcriptase activity: optimization, validation, and comparative analysis with other detection systems", *Journal of virological Methods* 61 (1996) pp. 135–143, Accepted May 3, 1996.

Sano et al., "Comparable sensitivities for detection of HIV–1 reverse transcriptase (RT) and other polymerases by RT assays requiring no radioisotopic materials", *Journal of Virological Methods* 53 (1995) pp. 235–244, Accepted Mar. 1, 1995.

Boni et al., "Sensitive Detection and Quantification of Particle–Associated Reverse Transcriptase in Plasma of HIV–1–Infected Individuals by the Product–Enhanced Reverse Trancriptase (PERT) Assay", *Journal of Medical Virology* 49:23–28 (1996).

Patience et al., "Human Endogenous Retrovirus Expression and Reverse Transcriptase Activity in the T47D Mammary Carcinoma Cell Line", *Journal of Virology,* Apr. 1996, pp. 2654–2657.

Havlir et al., "High–Dose Nevirapine: Safety, Pharmacokinetics, and Antiviral Effect in Patients with Human Immunodeficiency Virus Infection", *The Journal of Infectious Diseases* 1995; 171:537–45.

"Comparison of M–MLV Reverse Transcriptase and Tth Polymerase Activity in RT–PCR of Samples with Low Virus Burden", *BioTechniques,* vol. 17, No. 6 (1994), pp. 1035–1036.

"Reverse Transcriptase Microassay", A.G. Filler, Division of Biochemistry, St. George's Hospital Medical School, University of London, 1993 Packard Instrument Company, 800 Research Parkway, Menden, CT.

G. Duke et al.; "Sequence and structural elements that contribute to efficient encephalomyocarditis virus RNA translation"; *Journal of Virology;* Mar. 1992; pp. 1602–1609, Abstract Only.

METHODS FOR SENSITIVE DETECTION OF REVERSE TRANSCRIPTASE

CROSS REFERENCE TO RELATED APPLICATIONS

This application is a continuation of U.S. application Ser. No. 08/763,762, filed Dec. 11, 1996 now U.S. Pat. No. 5,849,494, which is a continuation-in-part of U.S. application Ser. No. 08/379,851, filed Jan. 27, 1995, now abandoned.

BACKGROUND OF THE INVENTION

1. Field of the Invention

The present invention provides a method for detecting the presence of a retrovirus in a biological sample by detecting the presence of the enzyme, reverse transcriptase. The method utilizes a template and primers in conditions under which a DNA strand is synthesized and subsequently amplified by the polymerase chain reaction, if reverse transcriptase is present.

2. Background Art

Retroviruses are widely distributed in vertebrates and are known to cause a variety of diseases in man and animals including immunodeficiencies, leukemias and lymphomas (1). The entire retrovirus family is characterized by the presence of a unique enzyme, reverse transcriptase (RT), which transcribes the viral genomic RNA into a double-stranded DNA copy (1). This feature has led to studies of the unique enzymatic function of RT for two main applications. First, the presence of RT has been the basis for diagnosis of retroviral infection and for the generic detection of the presence of retroviruses in cell cultures and in the infected host. Second, the RT enzyme constitutes a primary target for antiviral drug intervention (1,2).

The polymerase function of RT from several retroviruses has been well characterized and shown to require an RNA template, a primer, triphosphate, a divalent cation and physiological salts (1). Therefore, assays for RT activity have conventionally used these reagents and conditions to measure the ability of a sample to produce a DNA copy of a known exogenous RNA template (e.g., poly rA) by synthesizing a complementary DNA oligonucleotide primer with radiolabeled nucleotides (e.g., $^3$H- or $^{32}$P-dTTP). RT synthesized DNA has been detected by measuring incorporation of the labeled nucleotide (3,4) and more recently, by assays which employ nonradioactive nucleotides in enzyme linked immunosorbent assay (ELISA) formats have been developed (5–8) and by polymerase chain reaction (PCR) (17), as further described below.

Although RT assays continue to be an essential laboratory tool for the identification of known and novel retroviruses (4–11), the successful use of RT assays has been limited to the detection of retroviral particles in culture supernatant (4–8), which has the disadvantage of requiring that a virus be cultured before detection. By the present methods, lentiviruses, such as human immunodeficiency virus-1 (HIV-1) may be readily detected, but oncoviruses, such as human T lymphocytic virus types I and II (HTLV-I and HTLV-II), are much more difficult to detect, presumably because of poor RT activity and because they are typically cell-associated, which means their RT is less accessible for detection in culture supernatants (6–8). This limitation has rendered RT testing of little value in the detection of HTLV infection.

Despite multiple attempts to improve the sensitivity of RT assays, the direct detection of retroviruses in clinical samples (e.g., serum) has been unsuccessful (4–12). For example, in studies of HIV-1 infected individuals, detection of virus in plasma by RT assays has been largely abandoned because of the low sensitivity of this method (12).

The inability to detect RT activity in serum hinders the use of this virological marker in diagnosing disease, monitoring drug efficacy in patients, monitoring virus load and predicting disease progression. Present methods for qualitative and quantitative detection of plasma HIV-1 include viral isolation and p24 antigen capture (13–15). However, these assays have disadvantages. Virus isolation from plasma requires virus culture that is typically maintained for 14 to 28 days and is labor intensive, time consuming, fraught with biological variation and is not a universal marker in the infected population given the low levels of HIV-1 in patients with CD4+ T lymphocyte counts of >200/mm$^3$. Similarly, p24 antigen, either free, virion-associated, or immune complexed, is not always present in the HIV-1 infected population.

RT-PCR permits the qualitative detection of the cell-free virus in plasma using an exogenous RT and a primer pair of known sequence to amplify viral RNA sequences in the plasma (15,16). Although RT-PCR has been reported to be highly sensitive, this assay requires RNA extraction and multiple sample manipulations that may increase the risks of PCR contamination. The RT-PCR assay may be complicated further by the lack of a standardized universal quantitative test and the variabilities that may be incurred during processing and storage with regard to the degradation of the genomic RNA. Although RT-PCR, like antigen capture, is highly specific, a knowledge of the nucleotide sequence of the target retrovirus fragment is necessary for primer development. Given this limitation, RT-PCR is not suitable for detecting variant, novel, or unknown retroviruses.

Recently, two assays for RT, which use the RNA of bacteriophage MS2 or brome mosaic virus (BMV) as a template and PCR as a detection system, have been reported to be highly sensitive for the detection of murine leukemia virus RT and other stocks of retroviruses in serum (18,19). However, the evaluation of the specificity and the sensitivity of these assays on adequate numbers of serum specimens was not disclosed (18,19). In addition, in both of these assays, problems with inhibitors of RT activity in serum and nonspecific background RT activity have been described (20), raising serious questions about the diagnostic value of these assays.

This invention provides a RT assay that employs a PCR-based amplification system to detect a known cDNA product of the RT reaction. The assay of the present invention, referred to hereafter as Amp-RT, is highly sensitive and specific, requires no knowledge of viral genomic sequence and allows the detection of RT activity in samples of individuals infected with retroviruses or any other biological entity that produces RT.

SUMMARY OF THE INVENTION

The present invention provides a method for detecting the presence of a retrovirus in a biological sample comprising the steps of: a) contacting the biological sample with an RNA template and a complementary DNA primer under conditions whereby the RNA template and the DNA primer will anneal and a DNA strand will be synthesized as an extension from the DNA primer if reverse transcriptase is present in the sample; b) amplifying the synthesized DNA; and c) detecting the amplification of the synthesized DNA, the amplification of the synthesized DNA indicating the presence of reverse transcriptase in the biological sample, thus indicating the presence of a retrovirus in the biological sample.

The present invention also provides a method of detecting the presence of a retrovirus in a biological sample comprising the steps of: a) contacting the biological sample with an RNA template, wherein the RNA template is a suitable region of the encephalomyocarditis virus which consists of the ribonucleotide of SEQ ID NO:4 and a complementary DNA primer, wherein the primer is the oligonucleotide of SEQ ID NO:2, under conditions whereby the RNA template and the DNA primer will anneal and a DNA strand will be synthesized as an extension from the DNA primer if reverse transcriptase is present in the sample; b) amplifying the synthesized DNA, wherein the amplification is by the polymerase chain reaction method whereby the conditions for the amplification comprise 30–40 cycles of heating the synthesized DNA and a primer pair to 93 to 96° C. for 30 seconds to one minute, 53 to 56° C. for 30 seconds to one minute and 70 to 74° C. for 30 seconds to five minutes, wherein the primer pair consists of the oligonucleotide consisting essentially of SEQ ID NO:1 and the oligonucleotide consisting essentially of SEQ ID NO:2; and c) detecting the amplification of the synthesized DNA, wherein the detection of the amplification of the synthesized DNA is by Southern blot hybridization assay, with a probe consisting essentially of the oligonucleotide of SEQ ID NO:3, the amplification of the synthesized DNA indicating the presence of reverse transcriptase in the biological sample, thus indicating the presence of a retrovirus in the biological sample.

Additionally provided is a kit for detecting the presence of a retrovirus in a biological sample, comprising a suitable region of the encephalomyocarditis virus genome as an RNA template and a complementary DNA primer for reverse transcriptase and a primer pair for polymerase chain reaction, whereby each component is provided in separate containers or any combination of the components is provided in a single container.

DETAILED DESCRIPTION OF THE INVENTION

As used in the specification and in the claims, "a" can mean one or more, depending on the context in which it is used.

The present invention provides a method for detecting the presence of a retrovirus in a biological sample comprising the steps of: a) contacting the biological sample with an RNA template and a complementary DNA primer under conditions whereby the RNA template and the DNA primer will anneal and a DNA strand will be synthesized as an extension from the DNA primer if reverse transcriptase is present in the sample; b) amplifying the synthesized DNA; and c) detecting the amplification of the synthesized DNA, the amplification of the synthesized DNA indicating the presence of reverse transcriptase in the biological sample, thus indicating the presence of a retrovirus in the biological sample.

The RNA template can comprise a suitable region of any ribonucleotide sequence such as, for example, the encephalomyocarditis virus genome. As used herein, a "suitable region" means a region of the RNA sequence having no significant secondary structure, less than 50% G-C content and to which complementary DNA primers can be generated which have $T_m$ values within the range of reaction temperatures appropriate for the synthesis of a DNA strand, as further described herein. The RNA template can be of a length sufficient to produce a DNA product ranging in size from 100 to 500 base pairs in length and most preferably about 300 base pairs in length. The RNA template can be the ribonucleotide of SEQ ID NO:4.

As used herein, "complementary DNA primer" means an oligonucleotide which anneals to the RNA template in a particular orientation to allow for the synthesis of a nascent DNA strand in the presence of RT in the biological sample under the conditions described herein. Also as used herein, the "conditions" under which a DNA strand is synthesized include the presence of nucleotides, cations and appropriate buffering agents in amounts and at temperatures such that the RNA template and the DNA primer will anneal and oligonucleotides will be incorporated into a synthesized DNA strand if reverse transcriptase is present. More specifically, an example of these conditions is provided in the Examples section. The described conditions have been optimized from other known RT/cDNA synthesis protocols. It is generally known that other conditions can be established for optimization of a particular RT reaction on the basis of protocols well known to one of ordinary skill in the art. The DNA primer can be the reverse primer of a primer pair to be used in a subsequent amplification by PCR, such as, for example, the oligonucleotide of SEQ ID NO:2 (EMCR2).

The biological sample can comprise any biological tissue or body fluid (e.g., cells, serum, plasma, semen, urine, saliva, sputum, cerebrospinal fluid). The synthesized DNA strand can be amplified by any of the amplification protocols known in the art now or in the future, including but not limited to the polymerase chain reaction (PCR) (17), the ligation amplification reaction (LAR) (21), the ligase-based amplification system (LAS) (22), the self-sustained sequence replication (3 SR) system (23), the transcription-based amplification system (TAS) (24) and the Qβ replicase amplification method (25).

For amplification of the synthesized DNA by PCR, the conditions for amplification can include 30 to 40 (most preferably 35) cycles of heating the synthesized DNA and a primer pair to 93° to 96° C. (most preferably 95° C.) for 30 seconds to one minute (most preferably one minute), 53° to 56° C. (most preferably 55° C.) for 30 seconds to one minute (most preferably one minute) and 70° to 74° C. (most preferably 72° C.) for 30 seconds to five minutes (most preferably one minute).

As used herein, "a primer pair" refers to two primers, one having a forward designation and the other having a reverse designation relative to their respective orientations on a double-stranded DNA molecule which consists of a sense and antisense sequence, such that under the amplification conditions described herein, the forward primer anneals to and primes amplification of the sense sequence and the reverse primer anneals to and primes amplification of the antisense sequence. Primers can be selected for use in the amplification reaction on the basis of having less than 50% G-C content, having minimal complementarity with other primers in the reaction (to minimize the formation of primer dimers) and having $T_m$ values within the range of reaction temperatures appropriate for PCR. In addition, primers can be selected to anneal with specific regions of the RNA template such that the resulting DNA amplification product ranges in size from 100 to 500 base pairs in length and most preferably around 300 base pairs in length. For example, in the conditions described above, the primer pair can consist of the oligonucleotide of SEQ ID NO:1 (EMCF1) as the forward primer and the oligonucleotide of SEQ ID NO:2 (EMCR2) as the reverse primer.

As used herein, "detecting" or "detection" of the amplified DNA refers to quantitatively or qualitatively determining the presence of the amplified DNA strand which is only synthesized if RT is present in the biological sample. The amplification of the synthesized DNA can be detected by any method for the detection of DNA known in the art. For example, detection of the amplified DNA can be by Southern blot hybridization assay, by visualization of PCR products of specific molecular weight on ethidium bromide stained agarose gels, by measurement of the incorporation of radiolabeled nucleotides into the synthesized DNA strand by autoradiography or scintillation measurement, by ELISA modified for the capture of a detectable moiety bound to the amplified DNA, or any other detection method known to one of ordinary skill in the art.

For detection by Southern blot hybridization assay, the synthesized DNA can be detected by a probe specific for the DNA synthesized from the template. For example, such a specific probe can consist essentially of the oligonucleotide of SEQ ID NO:3 (EMCP1). A Southern blot hybridization protocol for use in the invention is demonstrated in the Examples.

The present invention provides a method for detecting the presence of a retrovirus in a biological sample comprising the steps of: a) contacting the biological sample with a suitable region of the encephalomyocarditis virus genome as an RNA template and a complementary DNA primer under conditions whereby the RNA template and the DNA primer will anneal and a DNA strand will be synthesized as an extension from the DNA primer if reverse transcriptase is present in the sample; b) amplifying the synthesized DNA; and c) detecting the amplification of the synthesized DNA, the amplification of the synthesized DNA indicating the presence of reverse transcriptase in the biological sample, thus indicating the presence of a retrovirus in the biological sample.

The present invention also provides a method of detecting the presence of a retrovirus in a biological sample comprising the steps of: a) contacting the biological sample with an RNA template and a complementary DNA primer under conditions whereby the RNA template and the DNA primer will anneal and a DNA strand will be synthesized as an extension from the DNA primer if reverse transcriptase is present in the sample; b) amplifying the synthesized DNA by the polymerase chain reaction method whereby the conditions for the amplification comprise 30–40 cycles of heating the synthesized DNA and a primer pair to 93 to 96° C. for 30 seconds to one minute, 53 to 56° C. for 30 seconds to one minute and 70 to 74° C. for 30 seconds to five minutes; and c) detecting the amplification of the synthesized DNA, the amplification of the synthesized DNA indicating the presence of reverse transcriptase in the biological sample, thus indicating the presence of a retrovirus in the biological sample.

The present invention further provides a method for detecting the presence of a retrovirus in a biological sample comprising the steps of: a) contacting the biological sample with a region of the encephalomyocarditis virus genome as an RNA template and a complementary DNA primer under conditions whereby the RNA template and the DNA primer will anneal and a DNA strand will be synthesized as an extension from the DNA primer if reverse transcriptase is present in the sample; b) amplifying the synthesized DNA by the polymerase chain reaction method whereby the conditions for the amplification comprise 30–40 cycles of heating the synthesized DNA and a primer pair to 93 to 96° C. for 30 seconds to one minute, 53 to 56° C. for 30 seconds to one minute and 70 to 74° C. for 30 seconds to five minutes; and c) detecting the amplification of the synthesized DNA, the amplification of the synthesized DNA indicating the presence of reverse transcriptase in the biological sample, thus indicating the presence of a retrovirus in the biological sample.

As an example, the present invention can provide a method for detecting a retrovirus in a biological sample comprising the steps of: a) contacting the biological sample with a suitable region of the encephalomyocarditis virus genome as an RNA template, wherein the RNA template is the ribonucleotide of SEQ ID NO:4 and a complementary DNA primer, wherein the primer is the oligonucleotide of SEQ ID NO:2, under conditions whereby the RNA template and the DNA primer will anneal and a DNA strand will be synthesized as an extension from the DNA primer if reverse transcriptase is present in the sample; b) amplifying the synthesized DNA, wherein the DNA is amplified by the polymerase chain reaction under conditions which comprise about 35 cycles of heating the synthesized DNA and a primer pair to 95° C. for one minute, 55° C. for one minute and 72° C. for one minute, wherein the primer pair consists of the oligonucleotide consisting essentially of the SEQ ID NO:1 and the oligonucleotide consisting essentially of the SEQ ID NO:2; and c) detecting the amplification of the synthesized DNA, wherein the amplification is detected by Southern blot hybridization assay with a probe consisting essentially of the oligonucleotide of SEQ ID NO:3.

Additionally provided is a kit for detecting the presence of a retrovirus in a biological sample, comprising the enzymes, buffering agents, cations and oligonucleotides well known in the art for carrying out RT and PCR reactions. The kit also comprises a suitable region of the encephalomyocarditis virus genome as an RNA template and a complementary DNA primer for reverse transcriptase and a primer pair for polymerase chain reaction. The RNA template, the complementary DNA primer and the primers of the primer pair can each be in separate containers or all or any combination of these components can be combined in a single container. The complementary DNA primer can be the oligonucleotide of SEQ ID NO:2 (EMCR2), the RNA template can be the ribonucleotide of SEQ ID NO:4 and the primer pair can consist of the oligonucleotide consisting essentially of SEQ ID NO:1 (EMCF1) and the oligonucleotide consisting essentially of SEQ ID NO:2 (EMCR2).

The present invention has additional applications based on the basic inventive principle that RT can be detected and quantitated in a biological sample. One application of this principle is the differential identification of retroviruses on the basis of the specific reactivity of the detected RT with antibodies against different retroviral RTs (for example, antibodies which can distinguish RT produced by HIV-1 or HIV-2 in infected individuals). Each retrovirus has a distinct RT, to which specific antibodies can be generated, thereby permitting identification of the specific retrovirus. The method of the present invention can be employed to first detect the presence of RT and various antibodies specific for RTs of different retroviruses can then be added to the biological sample to identify the type of retrovirus present. An antibody of known RT specificity will bind the RT present in the biological sample if the RT is produced by the virus to which the antibody is specific and will inhibit its activity, resulting in no DNA synthesis in the presence of antibody.

Another application of the present invention is screening patients for resistance to drug therapy. The susceptibility of RT to anti-RT drugs can be monitored over time in a patient receiving anti-RT drug therapy. The present invention can be employed to detect the emergence of anti-RT drug resistance in a patient by direct testing of the patient's serum for RT activity as an indicator of the susceptibility of the RT in the patient's serum to the anti-RT drug(s) used. If drug resistance is detected, alternative treatment strategies may be implemented. This invention obviates the need for the lengthy and labor-intensive culture methods currently used to study drug resistance in patients.

A third application of the present invention is the monitoring of virus load in patients infected with biological entities which produce RT. Quantitative measurement of RT over time can be correlated with survival and/or recovery rates in patients with illnesses caused by theses entities, for the purpose of following disease progression and prognosing the patient's illness.

The present invention is more particularly described in the following examples which are intended as illustrative only since numerous modifications and variations therein will be apparent to those skilled in the art.

EXAMPLES

The following examples are intended to illustrate, but not limit, the invention. While the protocols described are typical of those that might be used, other procedures known to those skilled in the art may be alternatively employed.

Viruses The retroviruses used in this study were prepared as follows. HIV-1 Lai and simian immunodeficiency virus (SIVB670) were propagated in peripheral blood lymphocytes (PBLs). Caprine arthritis encephalitis virus (CAEV-63) was propagated in fetal goat synovial membrane cells. HTLV-I and HTLV-II were obtained from supernatants of MT-2 and Mo-T cell lines; simian retroviruses types 1 and 2 (SRV-1 and SRV-2) were grown in Raji cells; gibbon ape leukemia virus (GALV) was grown in Jurkat cells and simian foamy virus type 3 (SFV-3) was grown in the Cf2Th cell line.

In Vitro Transcription of the RNA Template

An RNA sequence from the encephalomyocarditis virus (EMCV) was used as template and was generated from a plasmid vector obtained from Novagen (Madison, WI, USA). A small EMCV sequence (350 bp) (SEQ ID NO:4) was amplified from the plasmid, using standard PCR conditions and the primer pair T7-EMCF1 (SEQ ID NO:6) and EMCR2 (SEQ ID NO:2). The sequence of T7-EMCF1 (SEQ ID NO:6) was: 5'GGTACCTAATACGACTCACTATAGG-GAGACATTAGCCATTTCAACCCAT3' and that of EMCR2 (SEQ ID NO:2) was: 5'GTTCATGACAGGC-CGATACAGAGG3'.

To allow the in vitro transcription of this PCR product, the sense primer, EMCF1: 5'CATTAGCCATTTCAACCCAT3' (SEQ ID NO:1), was modified at the 5' end by adding a T7 promoter sequence: 5'GGTACCTAATACGACTCACTAT-3' (SEQ ID NO:5).

The EMCV-amplified product was then transcribed with the large scale T7 transcription kit from Novagen according to the manufacturer's instructions. The DNA in the RNA preparation was subsequently digested twice with 20 units of RNase-free DNase (Promega) at 37° C. for 60 minutes and the DNase was inactivated by heating at 95° C. for ten minutes. The purity of the RNA preparation was checked for residual DNA contamination by PCR amplification with EMCF1 (SEQ ID NO:1) and EMCR2 (SEQ ID NO:2) and subsequent Southern blot hybridization to the $^{32}$P-end-labeled internal probe EMCPI (SEQ ID NO:3): 5'TGCTCT-CACCTTATCAAAATCCAAT3'.

Amp-RT

Twenty ul or less of the biological sample to be tested was added to 40 l of RT buffer containing 10 ng of RNA template, 10 units of RNasin, 0.06% NP-40, 200 ng primer (EMCR2, SEQ ID NO:2), 0.8 mM EGTA, 2 mM DTT, 50 mM Tris-HCl, 5 mM KCl, and 10 mM MgCl$_2$. The reaction was incubated at 37° C. for two hours and then heated at 95° C. for ten minutes to inactivate any RT activity. A volume of 50 ul of standard PCR buffer (17) containing 0.5 units of Taq polymerase and 200 ng of the sense primer without the T7 sequence (EMCF1, SEQ ID NO:1) was added to this mixture. The reaction was cycled 35 times at 95° C. for one minute, 55° C. for one minute and 72° C. for one minute. Twenty ul of the reaction product was electrophoresed in 1.8% agarose gels and Southern blot hybridized to a $^{32}$P-end-labeled internal probe (EMCP1, SEQ ID NO:3) at 42° C. overnight. The blots were washed in 2×SSC (NaCl and sodium citrate), 0.5% sodium dodecyl sulfate (SDS) for one to two hours. The blots were exposed from six to 24 hours.

To check the integrity and the purity of the RNA template preparation, RT reactions were carried out using the EMCV RNA template (SEQ ID NO:4) and an HIV-1 virus stock as the RT source. While the HIV-1 reactions were positive, control reactions which had no HIV-1, or which were pretreated with RNase before the addition of HIV-1, were all negative. These negative results indicated that the underlying reaction of Amp-RT was RNA-dependent and that the RNA template and other assay components were free of any contaminating target DNA. To further confirm that the reaction was mediated by RT, Amp-RT reactions were prepared by using HIV-1 culture supernatant in the presence of 2 ug of tetrahydroimidazo-benzodiazepin (TIBO) compounds, which are non-nucleoside RT inhibitors (2). The results demonstrated inhibition of the Amp-RT reaction only in the presence of the TIBO compounds, while the DNA polymerase activity of Taq in the control amplification reactions was not affected.

Comparative Sensitivity Analysis of Amp-RT

Many specific and generic assays are currently used to detect the presence of retroviruses. To compare the relative sensitivities of these assays to Amp-RT, serial 10-fold dilutions of an HIV-1 culture supernatant were made in culture medium and then divided into equal aliquots. Separate aliquots were subjected to testing by standard RT assay, branched DNA detection, p24 antigen capture, 50% tissue culture infective dose (TCID$_{50}$) determination, RT-PCR and Amp-RT.

Standard RT Assay

RT activity was measured in culture supernatant with the template primer of poly(rA).oligo dT according to the methods of Willey et al. (3). The enzymatic activity was assessed by measuring the incorporated tritiated thymidine monophosphate.

Branched DNA (bDNA) Detection of HIV-1

Branched DNA (bDNA) detection of HIV-1 was performed according to the manufacturer's instructions (Chiron, Emryville, Calif., USA). A cutoff of 5,000 RNA equivalents/ml was used, as recommended by the manufacturer.

p24 Antigen Capture

Levels of base dissociated-p24 antigens of HIV-1 were determined by a commercially available ELISA kit from Organon Technika (North Carolina, USA).

TCID$_{50}$ Determination

The TCID$_{50}$ of the HIV-1 viral stock was determined on PBLs as previously described by McDougal et al. (26).

RT-PCR

Particle-associated HIV-1 genomic RNA in culture supernatant was extracted with phenouchloroform, precipitated with ethanol and reconstituted in 40 ul of RT buffer [50 mM Tris-Cl (pH 8.3), 20 mM KCl, 10 mM $MgCl_2$] (15). RNA was further digested with 5 units of DNase-I (Promega) in the presence of 10 mM sodium acetate at 37° C. for 30 minutes. DNase was inactivated by heating at 95° C. for ten minutes. For reverse transcription, 10 ul of RNA was added to 20 ul of the RT mixture, containing 10 mM DTT, 20 units RNasin, 0.875 mM each of GTP, ATP, CTP and TTP, 200 ng of reverse primer (SK39, SEQ ID NO:8) and 0.02 units of AMV-reverse transcriptase. The mixture was reverse transcribed at 42° C. for 45 minutes. Controls included 10 ul aliquots that were not reverse transcribed. All samples were then amplified by PCR in 100 ul reaction volumes for 35 cycles, using SK38/SK39 (SEQ ID NOS:7 and 8) as primers and the amplified products were Southern blot hybridized to the $^{32}$P-labeled SK19 (SEQ ID NO:9) probe (27).

The results, shown in Table 1, demonstrated that Amp-RT was the most sensitive assay and was 100,000 times more sensitive than the standard RT assay, 10,000 times more sensitive than the bDNA detection system and the p24 antigen capture assay and 100 times more sensitive than $TCHD_{50}$ and RT-PCR. The p24 concentration in the undiluted HIV-1 sample was found to be 1.6 ng.

Testing of Clinical Samples with Amp-RT

Forty-two serum samples from HIV-1 seropositive individuals enrolled in a study of the natural history of HIV in homosexual men in Atlanta, Ga., USA (28) were tested by Amp-RT. The clinical stage of the HIV-1 infection in these men was determined on the basis of the Centers for Disease Control and Prevention (CDC) revised classification system (29). Laboratory markers, including CD4+ lymphocyte counts and percentage of CD4+ lymphocytes in the blood, were determined by standard flow cytometric methods. Serum samples from 20 healthy individuals who were HTLV-I/II and HIV-1 seronegative were included as controls.

Preliminary experiments using normal human serum spiked with HIV-1 were all Amp-RT negative and indicated that preparation of serum samples for Amp-RT requires special conditions different from those described for culture supernatant. For instance, even small volumes (5–20 ul) of serum or plasma could not be directly tested by Amp-RT because of protein precipitation that develops during the high temperature stage of the PCR cycle. Therefore, to avoid this problem, sera were ultracentrifuged and the Amp-RT assay was performed using the viral pellet.

For testing of culture supernatant, 20 ul or less was used for the RT reaction. For testing serum or plasma samples, 0.5 ml was diluted 10-fold in DEPC-treated phosphate buffered saline, clarified by centrifugation at 1,000 g for 10 minutes and then ultracentrifuged at 44,000 g for one hour. The pellet was suspended in 50 ul of RT buffer containing 0.6% NP-40 for 15 minutes and aliquots of 5–45 ul were used in the Amp-RT assay.

The results of testing serum samples indicated that Amp-RT was able to detect RT activity in 36 (85.7% ) serum samples (Table 2), 31 of which (86.1%) had detectable p24 antigen. This high sensitivity was also coupled with a high specificity since none of the HIV-1/HTLV seronegative samples were positive. Of the six samples from patients classified as A1, three were Amp-RT positive (50%), while five of seven (71.4%) and 25 of 26 (96. 1%) of the samples from patients classified as B2 and C3, respectively, were Amp-RT positive.

Testing of the Hepatitis B Virus (HBV) by Amp-RT

Because the polymerase gene of HBV has been reported to possess RT-like activity (30), Amp-RT was employed to detect the HBV-associated RT activity. Serum samples from 21 HBV-infected individuals were selected, including 11 samples with detectable HBe antigen (Abbott HBe EIA, Chicago, USA) and ten other samples with no detectable HBe antigen. .

Despite the documented presence of HBV virions in 11 serum specimens, none of the samples yielded positive results by Amp-RT analysis. These negative results exclude the possibility of the HBV-associated RT interfering in the Amp-RT assay, at least under these conditions, and therefore confirm the specificity range of the assay for the detection of only retroviral RTs.

Detection of Different Retroviruses by Amp-RT.

The ability of Amp-RT to detect a wide variety of retroviruses representing members of all three retroviral subfamilies was investigated. The lentiviruses tested included HIV-1, SIV and CAEV. HTLV-I, HTLV-II, GALV, SRV-1 and SRV-2 were representative of the oncoviruses and SFV-3 was representative of the spumaviruses. Amp-RT was capable of detecting all retroviruses tested. Most importantly, viruses such as HTLV-I, HTLV-II and GALV, which are typically difficult to detect with the standard RT methodology, were easily identified with this assay.

These viruses could be detected by Amp-RT in dilutions containing 0.04 to 0.00004 ul of the original unconcentrated culture supernatant. The serial dilutions of the tested retroviruses were made in supernatant from uninfected cell lines (Hut-78, A301 or U937). All three supernatants consistently tested negative, as can be seen from the end point dilutions of the tested retroviruses.

Side by Side Comparison of Previously Published RT Assays

To demonstrate that the assay of the present invention provides increased specificity and sensitivity in comparison to other published RT assays [22,23], a side by side comparison of these assays can be performed. These assays differ in the particular RNA template sequence, primer sequences, RT buffer compositions, amplification conditions, detection conditions and sample preparation used. Therefore, for a comparison of the two assays, a panel of serum samples from HIV-1 seropositive individuals and from HIV-1 and HTLV-I/II negative individuals can be tested according to the teachings of the present assay and each other assay. Positive controls can include normal human serum spiked with HIV-1 virus particles. The specificity and sensitivity of these assays can then be computed and compared.

Throughout this application various publications are referenced by numbers within parentheses. Full citations for these publications are as follows. The disclosures of these publications in their entireties are hereby incorporated by reference into this application in order to more fully describe the state of the art to which this invention pertains.

The text of the Preliminary Amendment filed Dec. 11, 1996 in U.S. Ser. No. 08/763,762, now U.S. Pat. No. 5,549,494, is hereby incorporated by reference.

Although the present process has been described with reference to specific details of certain embodiments thereof, it is not intended that such details should be regarded as limitations upon the scope of the invention except as and to the extent that they are included in the accompanying claims.

TABLE 1

Comparison of the sensitivity of Amp-RT in the detection of HIV-1 with other generic and virus-specific methods.

| HIV-1 dilution | Std. RT | bDNA | p24 ag | $TCID_{50}$ | RT-PCR | Amp-RT |
|---|---|---|---|---|---|---|
| $10^{0}$ | + | + | + | + | + | + |
| $10^{-1}$ | + | + | + | + | + | + |
| $10^{-2}$ | + | + | + | + | + | + |
| $10^{-3}$ | − | + | + | + | + | + |
| $10^{-4}$ | − | − | − | + | + | + |
| $10^{-5}$ | − | − | − | + | + | + |
| $10^{-6}$ | − | − | − | − | − | + |
| $10^{-7}$ | − | − | − | − | − | + |
| $10^{-8}$ | − | − | − | − | − | − |

TABLE 2

Detection of RT activity by Amp-RT in serum samples from HIV-1 infected individuals characterized by clinical stage, CD4 + lymphocyte counts in the peripheral blood and amount of p24 antigen in the serum.

| No | Patient ID | p24 (pg/ml) | % CD4 | CD4 count | Clinical Stage* | Amp-RT |
|---|---|---|---|---|---|---|
| 1 | 69877 | NEG | 27 | 830 | A1 | NEG |
| 2 | 82850 | NEG | 23 | 699 | A1 | p |
| 3 | 69878 | 141 | 33 | 566 | A1 | P |
| 4 | 77913 | NEG | 25 | 599 | A1 | P |
| 5 | 111380 | 49 | 27 | 778 | A1 | NEG |
| 6 | 111318 | 49 | 28 | 539 | A1 | NEG |
| 7 | 85987 | 141 | 23 | 348 | A2 | P |
| 8 | 66583 | 55 | 13 | 286 | A2 | P |
| 9 | 62303 | 42 | 12 | 341 | B2 | P |
| 10 | 71172 | 56 | 22 | 281 | B2 | NEG |
| 11 | 71245 | 100 | 11 | 208 | B2 | P |
| 12 | 77149 | 44 | 16 | 282 | B2 | P |
| 13 | 86563 | 141 | 14 | 286 | B2 | P |
| 14 | 66994 | NEG | 25 | 260 | B2 | NEG |
| 15 | 57589 | 141 | 18 | 370 | B2 | P |
| 16 | 21149 | NEG | 10 | 97 | B3 | P |
| 17 | 70145 | 8 | 5 | 26 | C3 | NEG |
| 18 | 84300 | 141 | 1 | 4 | C3 | P |
| 19 | 111207 | N | 10 | 103 | C3 | P |
| 20 | 67365 | 141 | 5 | 24 | C3 | P |
| 21 | 96215 | 40 | 6 | 80 | C3 | P |
| 22 | 120979 | 141 | 3 | 19 | C3 | P |
| 23 | 20525 | 73 | 3 | 22 | C3 | P |
| 24 | 736 | 103 | 8 | 50 | C3 | P |
| 25 | 1837 | 158 | 3 | 6 | C3 | P |
| 26 | 3125 | 150 | 5 | 12 | C3 | P |
| 27 | 3369 | 33 | 1 | 1 | C3 | P |
| 28 | 20577 | 85 | 6 | 123 | C3 | P |
| 29 | 20525 | 73 | 3 | 22 | C3 | P |
| 30 | 20577 | 85 | 6 | 123 | C3 | P |
| 31 | 20709 | 158 | 10 | 42 | C3 | P |
| 32 | 20876 | 80 | 7 | 57 | C3 | P |
| 33 | 21156 | 124 | 14 | 106 | C3 | P |
| 34 | 21196 | 24 | 8 | 48 | C3 | P |
| 35 | 21684 | 45 | 4 | 25 | C3 | P |
| 36 | 23505 | 64 | 4 | 19 | C3 | P |
| 37 | 23507 | 15 | 3 | 52 | C3 | P |
| 38 | 24462 | 149 | 6 | 41 | C3 | P |
| 39 | 24705 | 149 | 5 | 128 | C3 | P |
| 40 | 25238 | 98 | 5 | 13 | C3 | P |
| 41 | 23209 | 71 | 5 | 10 | C3 | P |
| 42 | 53416 | NEG | 14 | 81 | C3 | P |

*A1 and A2 refer to asymptomatic, acute (primary) or persistent generalized lymphadenopathy with CD4+ lymphocyte counts of >500/ul or 200–499/ul, respectively. B2 and B3 refer to symptomatic conditions different from those in stage A or AIDS, with CD4+ lymphocyte counts of 200–499/ul and <200ul, respectively. C3 refers to AIDS, with CD4+ lymphocyte counts of <200/ul (29).

REFERENCES

1. Coffin, J. M. 1990. Retroviridae and their replication. In: Fields, B. N. et al., *Virology*, 2d Ed. Raven Press, New York.
2. Shinazi R. F. et al. 1992. Insights into HIV chemotherapy *AIDS Res. and Hum. Retroviruses* 8:963–990.
3. Willey, R. L. et al. 1988. In vitro mutagenesis identifies a region within the envelope gene for the human immunodeficiency virus that is critical for infectivity *J. Virol.* 62:139–147
4. Spira, T. J. et al. 1987. A micromethod for assaying the reverse transcriptase of HTLV-III/LAV *J. Clin. Microbiol.* 25:97–99
5. Eberle, J. et al. 1992. A new method of measuring reverse transcriptase activity by ELISA *J. Virol. Meth.* 40:347–356
6. Somogyi, P. A. et al. 1990. A solid phase reverse transcription micro-assay for the detection of human immunodeficiency virus and other retroviruses in cell culture supernatants *J. Virol. Meth.* 27:269–276
7. Cook, R. F. et al. 1991. A nonradioactive micro-assay for released reverse transcriptase activity of a lentivirus *Biotechniques* 13:380–386
8. Suzuki, K. et al. 1993. Detection of human immunodeficiency virus (HIV) by calorimetric assay for reverse transcriptase activity on magnetic beads *Biotechnol. Appl. Biochem.* 18:37–44
9. Petry, H. et al. 1992. Isolation and characterization of a retrovirus from the fish genus *Xiphorus Virology* 188:785–792
10. Phan-Thanh, L. et al. 1992. Porcine retrovirus: Optimal conditions for its biochemical detection *Arch. Virol.* 123:255–265
11. De las Heras et al. 1991. Enzootic nasal tumour of goats: Demonstration of a type D-related retrovirus in nasal fluids and tumours *J. Gen. Virol.* 72:2533–2535
12. Sano, K. et al. 1987. Antibody that inhibits human immunodeficiency virus reverse transcriptase and association with inability to isolate virus. *J. Clin. Microbiol.* 25:2415–2417
13. Kageyama, S. et al. 1988. An improved method for the detection of HIV antigen in the blood of carriers *J. Virol. Meth.* 22:125–131
14. Ho, D. D. et al. 1988. Quantitation of human immunodeficiency virus type 1 in the blood of infected persons *N. Eng. J. Med.* 321:1621–1625
15. Piatak, M. et al. 1993. High levels of HIV-1 in plasma during all stages of infection determined by competitive PCR *Science* 259:1749–1754
16. Mulder, J. et al. 1994. Rapid and simple PCR assay for quantitation of human immunodeficiency virus type 1 RNA in plasma: Application to acute retroviral infection *J. Clin. Microbiol.* 32:292–300
17. Innis, M. A. et al. 1990. *PCR Protocols: A Guide to Methods and Applications* Academic Press, San Diego, Calif.
18. Pyra, H. et al. 1994. Ultrasensitive retrovirus detection by a reverse transcription assay based on product enhancement *Proc. Natl. Acad. Sci. USA* 91:1544–1548
19. Silver, J. et al. 1993. An RT-PCR assay for the enzyme activity of reverse transcriptase capable of detecting single virions *Nuc. Acids Res.* 21:3593–3594
20. Silver, J. et al. 1994. Abstract from the Conference on Feasability of Genetic Technology to Close the HIV Window in Donor Screening, FDA, Maryland, Sep. 26, 1994

21. Wu, D. Y. et al. 1989. *Genomics* 4:560
22. Barringer, K. J. et al. 1990. *Gene* 89:117
23. Guatelli, J. C. et al. 1990. *Proc. Nail. Acad Sci.* USA 87:1874
24. Kwoh, D. Y. et al. 1989. *Proc. Nail. Acad. Sci.* USA 86:1173
25. Lizardi, P. M. et al. 1988. *Bio/Technology* 6:1197
26. McDougal, J. S. et al. 1985. Immunoassay for the detection and quantitation of infectious human retrovirus, lymphadenopathy-associated virus *J. Immunol. Meth.* 76:171–183
27. Ou, C. Y. et al. 1988. DNA amplification for direct detection of HIV-1 in DNA of peripheral blood mononuclear cells *Science* 239:295–297
28. Fishbein, D. B. et al. 1985. Unexplained lymphadenopathy in homosexual men-A longitudinal study JAMA 254:930–935
29. Centers for Disease Control and Prevention. 1992. Revised classification system for HIV infection and expanded surveillance case definition for AIDS among adolescents *Morbidity and Mortality Weekly Report* 41:1 –19
30. Bavand, M. et al. 1989. The hepatitis B virus-associated reverse transcriptase is encoded by the viral pol gene *J. Virol.* 63:1019–1021

What is claimed is:

1. A method of detecting the presence of a retrovirus in a body fluid sample comprising the steps of:
    a) contacting the sample with a region of the encephalomyocarditis virus genome as an RNA template and a complementary DNA primer under conditions whereby the RNA template and the DNA primer will anneal and a DNA strand will be synthesized as an extension from the DNA primer if reverse transcriptase is present in the sample;
    b) amplifying the synthesized DNA; and
    c) detecting the amplification of the synthesized DNA, the amplification of the synthesized DNA indicating the presence of reverse transcriptase in the sample, thus indicating the presence of a retrovirus in the sample.

2. The method of claim 1, wherein the complementary DNA primer is the oligonucleotide of SEQ ID NO:2.

3. The method of claim 1, wherein the synthesized DNA is amplified by the polymerase chain reaction.

4. The method of claim 3, wherein the synthesized DNA is amplified by the polymerase chain reaction and the conditions whereby the synthesized DNA is amplified comprise 30–40 cycles of heating the synthesized DNA and a primer pair to 93 to 96° C. for 30 seconds to one minute, 53–56° C. for 30 seconds to one minute and 70 to 74° C. for 30 seconds to five minutes.

5. The method of claim 1, wherein the conditions whereby the synthesized DNA is amplified comprise about 35 cycles of heating the synthesized DNA and a primer pair to about 95° C. for one minute, about 55° C. for one minute and about 72° C. for one minute.

6. The method of claim 1, wherein the primer pair consists of the oligonucleotide of SEQ ID NO:1 and the oligonucleotide of SEQ ID NO:2.

7. The method of claim 1, wherein the RNA template is the ribonucleotide of SEQ ID NO:4.

8. The method of claim 1, wherein the amplification of the synthesized DNA is detected by Southern blot hybridization assay.

9. The method of claim 8, wherein the amplification of the synthesized DNA is detected by Southern blot hybridization assay and the synthesized DNA is detected in the Southern blot hybridization assay with a probe of the oligonucleotide of SEQ ID NO:3.

10. A kit for detecting the presence of a retrovirus in a body fluid sample, comprising a suitable region of the encephalomyocarditis virus genome as an RNA template, a complementary DNA primer for reverse transcriptase, a primer pair for polymerase chain reaction, and a positive or negative control.

11. The kit of claim 10, wherein the complementary DNA primer is the oligonucleotide of SEQ ID NO:2.

12. The kit of claim 10, wherein the RNA template is the ribonucleotide of SEQ ID NO:4.

13. The kit of claim 10, wherein the primer pair consists of the oligonucleotide of SEQ ID NO:1 and the oligonucleotide of SEQ ID NO:2.

14. A DNA primer for amplifying DNA by the polymerase chain reaction where the primer is an isolated nucleic acid selected from the group consisting of the nucleotide sequence set forth in the Sequence Listing as SEQ ID NO:1, the nucleotide sequence set forth in the Sequence Listing as SEQ ID NO:2 and the nucleotide sequence set forth in the Sequence Listing as SEQ ID NO:10.

15. An RNA template for synthesizing DNA wherein the RNA template is an isolated nucleic acid consisting of the nucleotide sequence set forth in the Sequence Listing as SEQ ID NO:4.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CATTAGCCAT TTCAACCCAT                                          20

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GTTCATGACA GGCCGATACA GAGG                                24

(2) INFORMATION FOR SEQ ID NO:3:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

TGCTCTCACC TTATCAAAAT CCAAT                              25

(2) INFORMATION FOR SEQ ID NO:4:

(i) SEQUENCE CHARACTERISTICS:
      (A) LENGTH: 374 base pairs
      (B) TYPE: nucleic acid
      (C) STRANDEDNESS: single
      (D) TOPOLOGY: linear (ii) MOLECULE TYPE: RNA (genomic)

(xi) SEQUENCE DESCRIPTION: SEQ ID NO:4:

```
CAUUAGCCAU UUCAACCCAU GCGUUUGAGG AGAAGCGCUU UCUGAUAACC GGUGGUCUCC      60

CAUCAGGUUG UGCAGCGACC UCAAUGCUAA ACACUAUAAU GAAUAAUAUA AUAAUUAGGG     120

CGGGUUUGUA UCUCACGUAU AAAAAUUUUG AAUUUGAUGA UGUGAAGGUG UUGUCGUACG     180

GAGAUGAUCU CCUUGUGGCC ACAAAUUACC AAUUGGAUUU UGAUAAGGUG AGAGCAAGCC     240

UCGCAAAGAC AGGAUAUAAG AUAACUCCCG CUAACACAAC UUCUACCUUU CCUCUUAAUU     300

CGACGCUUGA AGACGUUGUC UUCUUAAAAA GAAAGUUUAA GAAAGAGGGC CCUCUGUAUC     360

GGCCUGUCAU GAAC                                                      374
```

(2) INFORMATION FOR SEQ ID NO:5:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

```
GGTACCTAAT ACGACTCACT AT                                              22
```

(2) INFORMATION FOR SEQ ID NO:6:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

```
GGTACCTAAT ACGACTCACT ATAGGGAGAC ATTAGCCATT TCAACCCAT                 49
```

(2) INFORMATION FOR SEQ ID NO:7:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:7:

```
ATAATCCACC TATCCCAGTA GGAGAAAT                                        28
```

(2) INFORMATION FOR SEQ ID NO:8:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:8:

```
TTTGGTCCTT GTCTTATGTC CAGAATGC                                        28
```

(2) INFORMATION FOR SEQ ID NO:9:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
ATCCTGGGAT TAAATAAAAT AGTAAGAATG TATAGCCCTA C                    41
```

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:10:

```
CTCCCATCAG GTTGTGCAGC GACC                                       24
```

(2) INFORMATION FOR SEQ ID NO:11:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:11:

```
CUCCCAUCAG GUUGUGCAGC GACCUCAAUG CUAAACACUA UAAUGAAUAA UAUAAUAAUU     60

AGGGCGGGUU UGUAUCUCAC GUAUAAAAAU UUUGAAUUUG AUGAUGUGAA GGUGUUGUCG    120

UACGGAGAUG AUCUCCUUGU GGCCACAAAU UACCAAUUGG AUUUUGAUAA GGUGAGAGCA    180

AGCCUCGCAA AGACAGGAUA UAAGAUAACU CCCGCUAACA CAACUUCUAC CUUUCCUCUU    240

AAUUCGACGC UUGAAGACGU UGUCUUCUUA AAAAGAAAGU UUAAGAAAGA GGGCCCUCUG    300

UAUCGGCCUG UCAUGAAC                                                  318
```